United States Patent [19]

Lubowsky et al.

[11] 4,405,300
[45] Sep. 20, 1983

[54] FURNACE TRAY WITH CARBON PLATE

[75] Inventors: Jack Lubowsky; Ronald Berger, both of East Brunswick, N.J.

[73] Assignee: Tri-Dynamics Dental Co., Inc., East Brunswick, N.J.

[21] Appl. No.: 238,976

[22] Filed: Feb. 27, 1981

[51] Int. Cl.³ .............. F24D 23/02; F27B 5/04; F27D 5/00
[52] U.S. Cl. ............................. 432/2; 432/198; 432/258; 432/259
[58] Field of Search ............... 432/2, 258, 259, 261, 432/265, 198

[56] References Cited

U.S. PATENT DOCUMENTS 1,573,543  2/1926  Fitzgerald .................. 432/258
3,958,924  5/1976  Egenoff et al. ............. 432/258
4,264,803  4/1981  Shinko ....................... 432/265

Primary Examiner—John J. Camby
Attorney, Agent, or Firm—Watson, Cole, Grindle & Watson

[57] ABSTRACT

A furnace tray for supporting tooth pegs used in the manufacture of false teeth, dental prostheses and the like comprises a refractory tray base member having a carbon plate receiving recess in its upper surface. A carbon plate is positioned in the recess and dental prostheses supported by tooth pegs are placed on the upper surface of the plate. The tray with the carbon plate and the dental prostheses thereon are then placed in a furnace and the teeth are fired. During the firing process the interior of the furnace is simultaneously purged by the carbon.

7 Claims, 2 Drawing Figures

U.S. Patent    Sep. 20, 1983    4,405,300
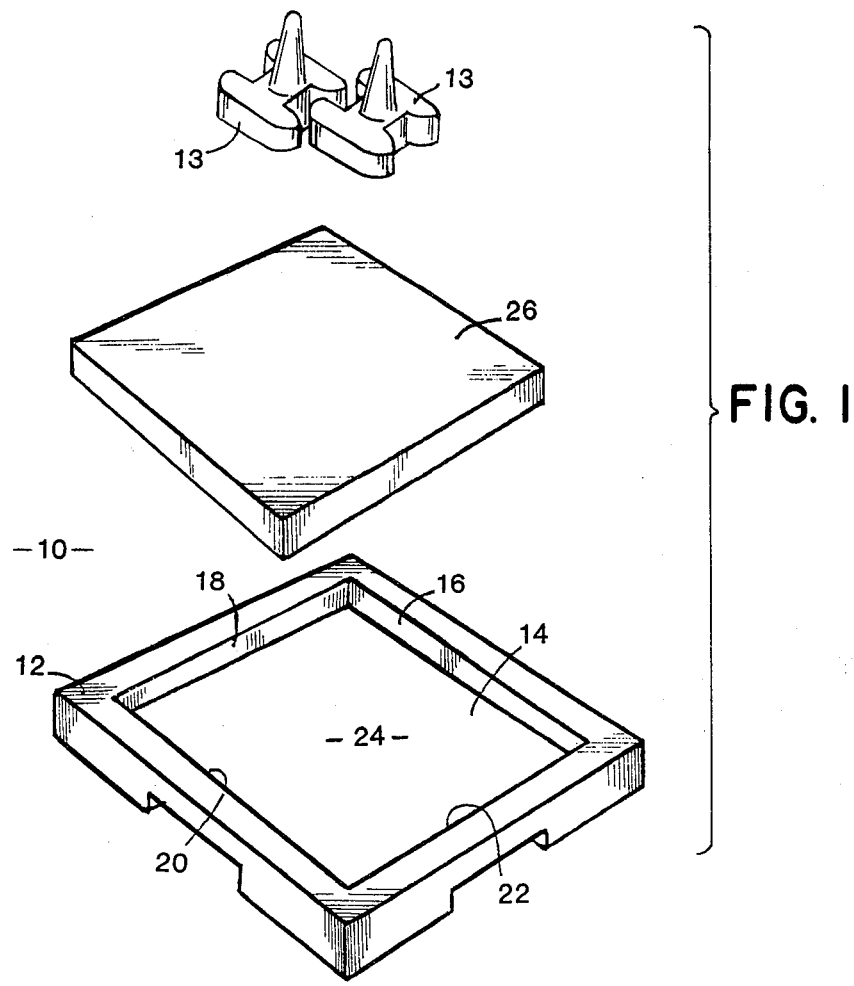
FIG. 1
FIG. 2
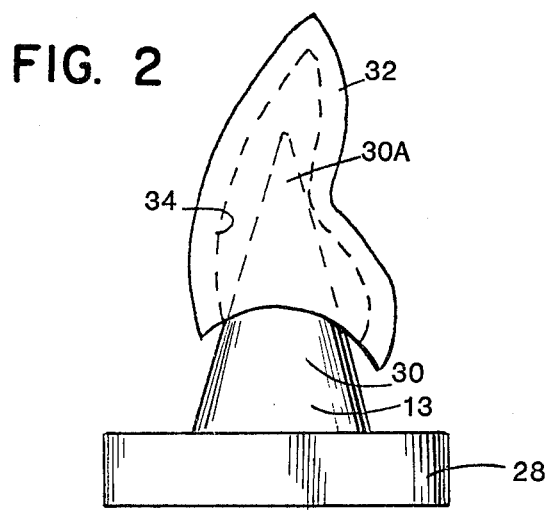

FURNACE TRAY WITH CARBON PLATE

BACKGROUND OF THE INVENTION

1. Field of the Invention

The present invention relates to the field of dental prostheses manufacturing and in particular to an improved method and firing tray facilitating purging of the furnace during the firing to minimize discoloration of the dental prostheses by contamination in the furnace.

2. Description of the Prior Art

In the manufacture of dental prostheses, a layer of ceramic material is generally placed over a base of precious metal and the composite is baked in a furnace. The teeth, which are generally hollow, are placed on pegs, which resemble inverted cones, and which in turn sit on trays of ceramic materials. Several teeth, either individually or as bridges, may be fired simultaneously as a single tray load.

As the price of precious metals has risen, dental labs have sought to use semi-precious metals, e.g, palladium-silver, as substitutes for gold. Unfortunately, the use of such metals results in discoloration of the teeth. This discoloration has been termed "greening" by those skilled in the art. The greening process is not at all well understood, but it is generally believed, by the routineers in the field, that semi-precious metal alloys emit a vapor, such as silver vapor, which contaminates the tooth directly and/or contaminates the interior of the furnace. This contamination produces aesthetically undesirable results by randomly staining the surface of the porcelain during the firing cycle.

There are currently in use, with varying degrees of success, a number of technical procedures for reducing the incidence of greening, including scrubbing, purging the furnace, etc. None of these known procedures, however, has been totally effective.

The most important of the prior procedures involves the use of carbon as an absorbant. After a number of firing cycles involving dental prostheses which comprise semi-precious metals, the furnace becomes contaminated. The carbon is placed in such an empty, contaminated furnace and the furnace is operated through a complete firing cycle. The carbon acts to absorb contamination from the furnace and the furnace is thus "cleansed" or "purged" so that it becomes suitable for subsequent firing of teeth. Such known method is generally effective; however, it is inconvenient and inefficient since the furnace and the technician periodically must be occupied with the non-productive firing cycles. Also, these previous procedures create a cyclic nature to the greening problem and presumably the greening of the procelain of the dental prostheses produced in the furnace just prior to purging of the furnace is more severe than it is just subsequent to the purging operation. Thus, the quality of the teeth produced varies with time. That is to say, between cleaning cycles the furnace gets dirtier and dirtier.

SUMMARY OF THE INVENTION

The problems encountered in the prior art as described above are minimized, if not substantially eliminated, through the use of the present invention, which provides a novel furnace tray for supporting tooth pegs used in the manufacture of dental prostheses and the like. The tray comprises a refractory tray base member having a upper support surface, there being a carbon plate mounted on the surface. When such furnace tray is utilized in the production of teeth, the interior of the furnace is purged and cleansed by the carbon plate simultaneously with the firing of the teeth. This eliminates the necessity for the use of a non-productive firing cycle. And moreover, the quality of the dental prostheses produced is more closely controlled and varies to a much lesser degree.

In a more specific aspect of the invention, the base member is constructed to include means defining a recess in the upper surface thereof for retaining the carbon plate. In particular, the walls of the recess should circumscribe the entire carbon plate so that as the latter disintegrates during normal use, the messy black powder thus created will be contained in the recess.

The present invention also provides a method for firing dental prostheses which comprises supporting dental prostheses to be fired on the upper surface of a carbon plate in a furnace. The teeth are fired while the same are supported by the carbon plate and the interior of the furnace is simultaneously purged with the carbon. Again, in its preferable form, the method of the invention includes the step of confining the carbon plate in a recess in an upper surface of a refractory tray base member during the firing step so that when the carbon plate disintegrates during normal operation, the black powder will be contained for easy removal from the furnace.

In yet another sense, the present invention provides a method for firing dental prostheses which comprises providing a furnace tray having a recess in its upper surface, arranging a quantity of carbon in the recess, supporting dental prostheses to be fired on the tray, placing the tray with the carbon and the dental prostheses thereon into a firing furnace, and firing the teeth in the furnace while simultaneously purging the interior of the furnace with the carbon.

BRIEF DESCRIPTION OF THE DRAWINGS

FIG. 1 is an exploded isometric view of a furnace tray constructed in accordance with the concepts and principles of the present invention; and FIG. 2 is an enlarged elevational view of a tooth peg for supporting a hollow dental prosthesis during the firing process.

DETAILED DESCRIPTION OF THE INVENTION

With reference to FIG. 1, the reference numeral 10 designates a furnace tray for supporting tooth pegs 13 used in the manufacture of dental prostheses and the like. The furnace tray 10 comprises a refractory tray base member 12 having an upper support surface 14. Base member 12 includes wall means 16, 18, 20 and 22 which define an upwardly opening recess 24 in member 12.

The furnace tray of the present invention also includes a carbon plate 26. Although the furnace tray is shown in an exploded condition in FIG. 1, it should be understood that the carbon plate 26 is normally disposed in recess 24. And as can be seen, walls 16, 18, 20 and 22 which define recess 24 normally circumscribe the entire carbon plate 26.

Since plate 26 is normally disposed in recess 24, it is desirable that the plate be of substantially the same size and shape as the recess. And in the preferred form illustrated in FIG. 1, the plate 26 and the recess 24 are rectangular in shape. Also, the walls 16, 18, 20 and 22 are preferably vertical walls for appropriately confining plate 26.

Normally, plate 26 will be disposed in recess 24 and tooth pegs 13 will be supported on plate 26. The manner in which pegs 13 operate to support dental prostheses is illustrated in FIG. 2. There it can be seen that each tooth peg 13 comprises a base element 28 and an upstanding conical portion 30. A tooth 32 supported by peg 13 has a hollow 34 therein which receives upper end 30*a* of conical portion 30. Thus, tooth 32 is supported for firing without contact between the outer surfaces of the tooth to be fired and the support therefor.

For purposes of the present invention, carbon plate 26 may be formed from any suitable carbon. And a number of suitable carbons are known to those skilled in this art. Preferably, however, it has been found that carbon plates cut from 3 inch diameter rod stock are very suitable for the purposes of the present invention. Unmachined industrial carbon rod stock produced by Union Carbide under the designation "Grade AGSR" has been found to be particularly useful. This rod stock is purchased in 3 inch diameters and is cut into the rectangular shapes illustrated in FIG. 1. Grade AGSR rod stock, as produced by Union Carbide, is a general purpose extruded graphite which has good resistance to thermal shock, excellent dimensional stability, good electrical and thermal conductivity and good mechanical strength. The maximum grain size is 0.03 inches and the bulk density of the carbon is 1.60 g/cc.

Base member 12 and the pegs 13 are of course formed from a refractory material suitable for withstanding the temperatures necessary to fire the ceramic outer layer of the dental prostheses.

In operation, carbon plate 26 is disposed in recess 24 and one or more pegs 13, each supporting a tooth 32 to be fired, are supported by plate 26. Tray member 12 with carbon plate 26 and teeth 32 thereon is then placed in a firing furnace and the teeth are fired. During the firing process, the interior of the furnace is simultaneously purged due to the presence of the carbon in carbon plate 26.

As will be appreciated by those skilled in the art to which the present invention relates, the carbon utilized for purging the interior of the furnace has a tendency to slowly disintegrate to present a non-integral batch of messy black powder. Such powder is very difficult to remove from the furnace. However, when the preferred form of the present invention is utilized, the messy black powder formed during the disintegration of plate 26 is confined within the recess 24. Accordingly, when the tray is removed from the furnace, it is a simple matter to dispose of the messy black carbon powder.

Through the use of the present invention it can be seen that the necessity for separately cleaning the furnace to avoid greening of the dental prostheses procelain has been obviated. Thus, when the present invention is utilized, it is no longer necessary to put the firing furnace through a non-productive firing cycle. Moreover, the carbon plate operates to continually clean the furnace during each firing cycle and therefor the quality of the fired dental prostheses remains consistent.

We claim:

1. A furnace tray for supporting tooth pegs used in the manufacture of dental protheses and the like comprising
    a generally plate-like tray base member which has an upper support surface, said upper support surface including an upwardly open recess having a blind bottom and side walls, and
    a carbon plate mounted in said recess, said carbon plate having a top face, a bottom face and side faces, said side faces being circumscribed by the side walls of said recess and said top face being exposed so as to mount thereon the tooth pegs.

2. A furnace tray as set forth in claim 1 wherein said recess and said carbon plate are of substantially the same size and shape.

3. A furnace tray as set forth in claim 2 wherein said recess and said plate are rectangular.

4. A furnace tray as set forth in claim 10 wherein said side walls of said recess are perpendicular with respect to the blind bottom.

5. A method for firing false teeth comprising:
    supporting false teeth to be fired on the upper surface of a carbon plate in a furnace; and
    firing said teeth while the same are supported by said carbon plate and thereby simultaneously purging the interior of the furnace with the carbon.

6. A method as set forth in claim 5 wherein is included the step of confining said carbon plate in a recess in an upper surface of a refractory tray base member during said firing step.

7. A method for firing dental prostheses comprising:
    providing a furnace tray having a recess in its upper surface;
    arranging a carbon plate in said recess;
    supporting dental prostheses to be fired on the tray;
    placing the tray with the carbon plate and false teeth thereon in a firing furnace; and
    firing the teeth in the furnace while simultaneously purging the interior of the furnace with carbon from the carbon plate.

* * * * *